US010527550B2

(12) United States Patent
Gebetsroither et al.

(10) Patent No.: US 10,527,550 B2
(45) Date of Patent: Jan. 7, 2020

(54) METHOD AND MICROPLATE READER FOR INVESTIGATING BIOLOGICAL CELLS OR CELL CULTURES

(71) Applicant: TECAN TRADING AG, Mannedorf (CH)

(72) Inventors: Harald Gebetsroither, Grodig (AT); Andreas Gfrorer, Konigsdorf (DE); Juha Koota, Berchtesgaden (DE)

(73) Assignee: TECAN TRADING AG, Mannedorf (CH)

( * ) Notice: Subject to any disclaimer, the term of this patent is extended or adjusted under 35 U.S.C. 154(b) by 0 days.

(21) Appl. No.: 13/800,467

(22) Filed: Mar. 13, 2013

(65) Prior Publication Data

US 2013/0280748 A1 Oct. 24, 2013

Related U.S. Application Data

(60) Provisional application No. 61/610,647, filed on Mar. 14, 2012.

(30) Foreign Application Priority Data

Mar. 14, 2012 (CH) ........................ 0365/12

(51) Int. Cl.
*G01N 21/64* (2006.01)
(52) U.S. Cl.
CPC ............... *G01N 21/6486* (2013.01)
(58) Field of Classification Search
None
See application file for complete search history.

(56) References Cited

U.S. PATENT DOCUMENTS 5,784,152 A 7/1998 Heffelfinger et al.
5,885,840 A * 3/1999 Kamentsky ........ G01N 15/1475
356/317

(Continued)

FOREIGN PATENT DOCUMENTS

DE 199 16 748 10/2000
DE 10236029 2/2004

(Continued)

OTHER PUBLICATIONS

Ker et al., PLoS One 6(11): e27672 (2011).*

(Continued)

*Primary Examiner* — Erin M. Bowers
(74) *Attorney, Agent, or Firm* — Notaro, Michalos & Zaccaria P.C.

(57) ABSTRACT

A method for investigating biological cells or cell cultures in a microplate reader receives at least one microplate with wells containing biological cells or cell cultures by a receiving device; positions the wells with respect to measuring devices of the microplate reader and detects integral measurement signals by at least one of the measuring devices. The biological cells or cell cultures in the specific wells of the microplate(s) are transilluminated by an illumination source of the microplate reader and imaged by an imaging camera. Each of the detected integral signals is compared with the image of the biological cells or cell cultures in the corresponding wells of the microplate(s) by a processor and is related to the imaged number, adherence, confluence or morphology of these biological cells or cell cultures.

18 Claims, 3 Drawing Sheets

(56) References Cited

U.S. PATENT DOCUMENTS

| | | |
|---|---|---|
| 6,673,595 B2 | 1/2004 | Barbera-Guillem |
| 6,730,901 B1 | 5/2004 | Rushbrooke |
| 7,782,454 B2 | 8/2010 | Zimenkov et al. |
| 2003/0103662 A1* | 6/2003 | Finkbeiner ............ G01N 21/253 382/128 |
| 2003/0127609 A1* | 7/2003 | El-Hage ................ G01N 21/253 250/574 |
| 2005/0051723 A1 | 3/2005 | Neagle et al. |
| 2005/0196325 A1 | 9/2005 | Bathe |
| 2005/0213374 A1 | 9/2005 | Xu et al. |
| 2006/0094868 A1* | 5/2006 | Giuliano ............ C07K 14/4721 536/23.2 |
| 2007/0177149 A1 | 8/2007 | Aronkyto |
| 2008/0212866 A1 | 9/2008 | Lett |
| 2012/0034569 A1 | 2/2012 | Sakamoto |
| 2012/0064564 A1 | 3/2012 | Grassl et al. |
| 2012/0153188 A1 | 6/2012 | Barrett et al. |
| 2012/0300194 A1 | 11/2012 | Zimenkov et al. |

FOREIGN PATENT DOCUMENTS

| | | |
|---|---|---|
| EP | 2253983 | 11/2010 |
| IT | MI 912510 | 3/1993 |
| JP | 58062542 | 4/1983 |
| JP | 11037923 | 2/1999 |
| WO | WO 99/39184 | 8/1999 |
| WO | WO 2006/031537 | 3/2006 |
| WO | WO 2008/117031 | 10/2008 |

OTHER PUBLICATIONS

European Search Report for EP13159032 filed on Mar. 13, 2013.
Wikepedia, "Lichtquelle", May 18, 2018, see attached statement for relevancy.

* cited by examiner

Fig. 5A
Fig. 5B
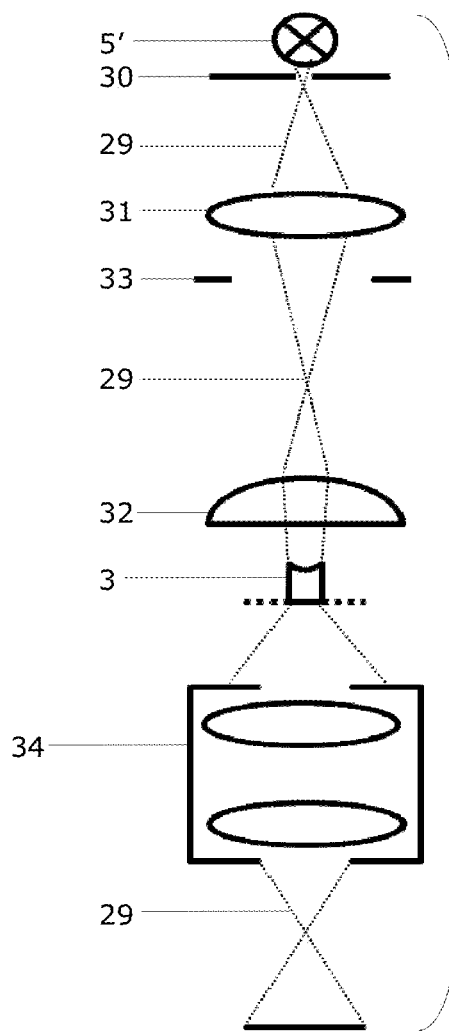
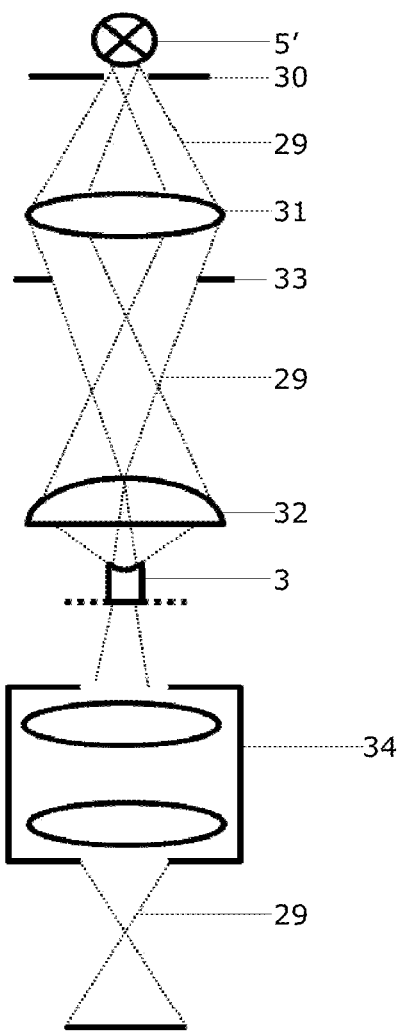
Fig. 5C
Fig. 5D
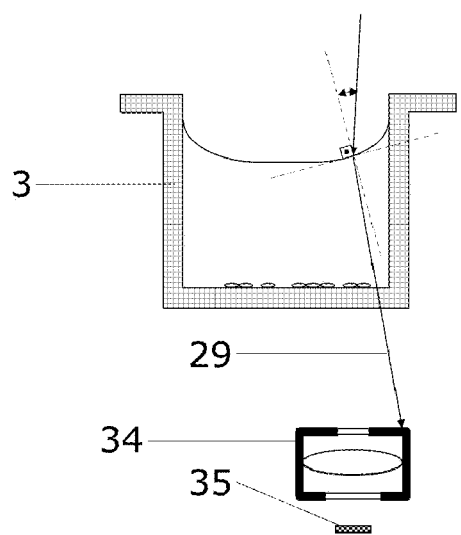
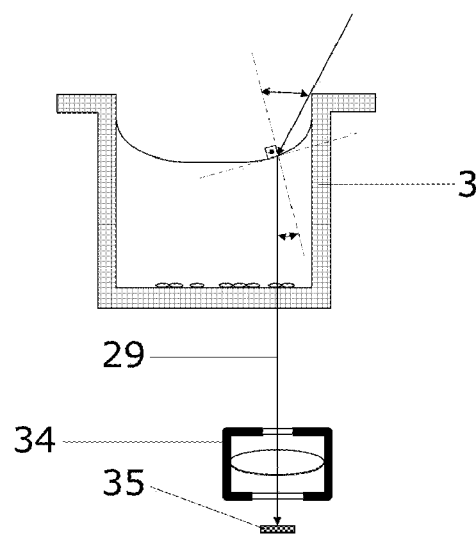

METHOD AND MICROPLATE READER FOR INVESTIGATING BIOLOGICAL CELLS OR CELL CULTURES

RELATED PATENT APPLICATIONS

This patent application claims priority of the U.S. Provisional Application No. 61/610,647, filed on Mar. 14, 2012 and of the Swiss patent application No. 00365/12, also filed on Mar. 14, 2012. The whole content of these two priority establishing applications is herein incorporated in its entirety by explicit reference.

RELATED FIELD OF TECHNOLOGY

The invention relates to a method for investigating biological cells or cell cultures in a microplate reader. This method typically comprises receiving at least one microplate with wells containing biological cells by means of a receiving device of the microplate reader; positioning the receiving device with the wells of the microplate(s) containing biological cells with respect to measuring devices of the microplate reader and detecting at least one integral signal (e.g. luminescence of all samples in one well of a microplate) by means of at least one of the measuring devices.

In addition it can be provided positioning the receiving device with the wells of the microplate(s) containing biological cells with respect to action sources of the microplate reader; bringing about an interaction between at least one of these action sources and biological cells in specific wells of the microplate(s) with at least one of the action sources to bring about or generate a measurable signal and detecting and detecting at least one integral signal (e.g. fluorescence or absorbance of all samples in one well of a microplate) which was brought about or generated by the action source(s) in or on biological cells in specific wells of the microplate(s).

RELATED PRIOR ART

Measurement of the fluorescence of cells or their metabolic products is known from the prior art. Thus, EP 2 253 983 A2 discloses a scanning microscope for the spectral detection of the emitted fluorescence of samples which are excited with a laser and are fed to a scattering grating split into different wavelength ranges and fed to a multi-anode photomultiplier tube. The document ITMI 912510 A1 discloses a so-called microplate reader with which samples in wells of microplates are irradiated with polarized light and the likewise polarized fluorescence light thereby triggered is detected with a photomultiplier tube. Microplate readers operating with non-polarized exciting light have also been known for a long time.

Documents are also known (e.g. JP 58 062 542 A or JP 11 037 923 A), which disclose the imaging of cohesion patterns of particles or biological cells on the bottom of wells of microplates by means of a digital camera which comprises an imaging CCD—(=Charge Coupled Device) or CMOS—(=Complementary Metal Oxide Semiconductor) sensor.

The detection of the luminescence of cells in wells of microplates is known, for example, from DE 102 36 029 A1. A dispenser by which means luminescence is triggered by adding liquids to the samples in the wells of a microplate and a CCD camera with which the luminescence emerging through the transparent bottoms of the microplate wells is photographed via an optical system is disclosed.

Known from WO 2006/031537 A2 is a method and an apparatus for investigating biological cells in microplates. The microplate is illuminated in a target region and the light coming from the target regions is guided to an array detector which detects discrete targets within the microplate wells in the target region as partial images and which combines the partial images to form an entire image of the microplate wells. In this case, cellular microarrays or also unordered biological cells can be detected.

The counting of biological cells in special slides configured as counting chambers has been known for a long time from the field of counting blood cells with the optical microscope. Automated cell counting systems or "cell counters" of different manufacturers are also known. These cell counters are in particular characterized in that a counting chamber with biological cells can be inserted into the counting system, whereupon the counting system automatically focuses the counting optics, counts the biological cells and displays the counting result.

Typically in laboratories which carry out investigations on biological cells or cell cultures in microplates, luminescence induced by light or electrically is produced, and this luminescence is measured with a photomultiplier tube or a semiconductor photomultiplier or imaged with an imaging camera. To interpret the measurement results or the images, the microplate is investigated by means of an optical microscope and it is determined whether the biological cells are still in a normal physiological state or whether they have an abnormal form or have even died.

A cell measuring device is also available on the market (IsoCyte Laser Scanning Cytometer, Molecular Devices, Sunnyvale, Calif., USA), which scans the biological cells in the wells of microplates with a laser beam and at the same time detects fluorescence or scattered signals generated by the laser beam by means of one or more photomultipliers, and which identifies and counts the biological cells present in a well and produces an image of the scanned well. By means of image processing the individual cells in each image are identified and their activity listed. The results of all the cells of a well can be integrated.

OBJECT AND SUMMARY OF THE PRESENT INVENTION

It is the object of the present invention to propose an alternative method for investigating biological cells or cell cultures in microplates and a suitable apparatus for carrying out the method.

This object is solved according to a first aspect with the features as herein disclosed by means of a method for investigating biological cells or cell cultures in a microplate reader. The method comprises the steps:
a) receiving at least one microplate with wells containing biological cells or cell cultures by means of a receiving device of the microplate reader;
b) positioning the receiving device with the wells of the microplate(s) containing biological cells or cell cultures with respect to measuring devices of the microplate reader; and
c) detecting at least one integral signal in or on biological cells or cell cultures in the specific wells of the microplate(s) by means of at least one of the measuring devices.

The method according to the invention is characterized in that the biological cells or cell cultures in the specific wells of the microplate(s) are transilluminated by means of an illumination source of the microplate reader, that transmission images of the biological cells or cell cultures in these specific wells of the microplate(s) are created by means of an imaging camera of the microplate reader, and that each of the detected integral signals is compared with the image of the biological cells or cell cultures in the corresponding wells of the microplate(s) by means of a processor and is related to the imaged number, adherence, confluence or morphology of these biological cells.

This object is solved according to a second aspect with the features as herein disclosed by means of a microplate reader for use in the method according to the invention for investigating biological cells or cell cultures. In this case, the microplate reader comprises:

a) a receiving device for receiving at least one microplate with wells containing biological cells or cell cultures and for positioning the microplate(s) with the wells containing biological cells or cell cultures with respect to measuring devices of the microplate reader; and b) at least one measuring device for detecting at least one integral signal that exists or was brought about or produced in or on biological cells or cell cultures in the specific wells of the microplate(s).

The microplate reader according to the invention is characterized in that it additionally comprises an illumination source for illuminating and an imaging camera for imaging the cells or cell cultures in these specific wells of the microplate(s) as well as a processor which is configured for comparing each of the detected integral signals with the image of the biological cells or cell cultures in the corresponding wells of the microplate(s) and for relating these integral signals to the imaged number, adherence, confluence or morphology of these biological cells or cell cultures.

Additional further developments of the method according to the invention or the microplate reader according to the invention and further features according to the invention are herein disclosed as well.

Advantages of the method according to the invention or the apparatus according to the invention comprise:

Hitherto two different devices, a microplate reader and an imaging microscope, were required for the combination of quantitative measurements of cell parameters in microplate readers with microscopic images for qualitative inspection of the status of these cell cultures. The present invention now makes it possible to carry out these two complementary investigations in one and the same device.

Hitherto, the microplates with the cell cultures had to be taken from the microplate reader and transferred to the microscope. This cumbersome step had to be carried out by an operator and additionally requires a certain time delay between the investigation methods. The present investigation now makes it possible to automate the combination of these two complementary investigations in a single device and with the shortest possible time differences between the detection of an integral signal in a specific microplate well and the imaging of this microplate well.

Hitherto, for transferring the microplates from a microplate reader to a microscope, the sensitive cell cultures were frequently exposed to the prevailing ambient conditions or had to be inconveniently shielded from these. The present invention preferably makes it possible to maintain a controlled atmosphere in the microplate wells with the cell cultures whilst carrying out all the quantitative and qualitative investigations on these biological cells.

In the microplate reader according to the invention, which is suitable for carrying out the method according to the invention, a module with imaging properties is integrated so that biological cells and cell cultures which are located, for example, on the bottom of the microplate well can be visualized with microscopic resolution.

In a preferred embodiment, the microplate reader according to the invention is configured as a multimode reader and allows an almost arbitrary and preferably automated combination of the detection of integral signals such as fluorescence, luminescence, absorbance, impedance or impedance variation in selected microplate wells with the microscope imaging of these microplate wells.

By determining the number of cells in a microplate well, it is possible to determine the average cell activity and therefore the difference between a changed cell activity and a changed cell number in this microplate well.

By determining the adherence or the fixing but also the morphology of the cells or cell cultures on the bottom of a microplate well, it is possible to draw conclusions on the physiological state of the cells.

Integral signals such as fluorescence, luminescence, absorbance, impedance or impedance variation serve for the measurement of cell activities. Variations of the intensity of these signals depend on variations of the cell activity as well as on variations of the number of cells (e.g. depending on cell propagation). Determination of the number of cells provides for normalization of the integral signal with the cell number and thus for an unbiased, automated capture of the cell activity.

Determining the confluence of the cells or cell cultures on the bottom of a microplate well reproduces the ratio of the bottom surface covered by a cell culture to the still-free bottom surface of this microplate well. This ratio again allows for normalization of the integral signal related to cell cultures with adherent cells with cell growth and thus for an unbiased, automated capture of the cell activity.

BRIEF DESCRIPTION OF THE ATTACHED DRAWINGS

The method according to the invention for investigating biological cells or cell cultures in a microplate reader and the corresponding microplate reader are now explained in detail by means of schematic drawings which show selected exemplary embodiments and are not intended to restrict the scope of the invention.

In the Figures:

FIG. 5 shows a schematic representation of the light path of the transillumination through a well of a microplate, wherein:

FIG. 5A shows conventional transillumination with sketched path of the transmitted light beam bundle;

FIG. 5B shows inventive transillumination with sketched path of the transmitted light beam bundle;

FIG. 5C shows conventional transillumination with sketched path of a transmitted light beam;

FIG. 5D shows inventive transillumination with sketched path of a transmitted light beam;

FIG. 6 shows pictures of a well in transillumination; wherein:

FIG. 7 shows the distribution of the intensity across a whole diameter of the wells in the pictures of FIG. 6; wherein:

DETAILED DESCRIPTION OF THE PRESENT INVENTION

Figure 1:
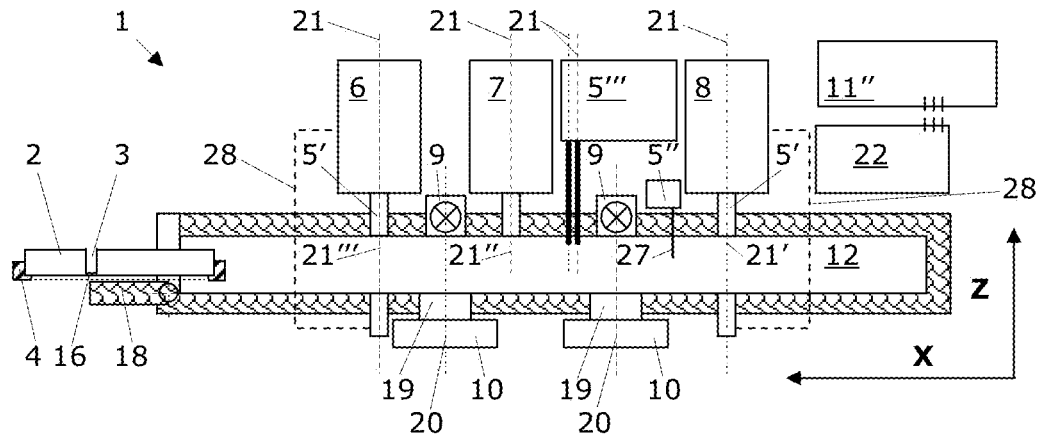
FIG. 1 shows a vertical section through a microplate reader according to a first embodiment during insertion of a microplate into the sample chamber which is preferably configured as a chamber which can be closed in a lightproof manner.

FIG. 1 shows a vertical section through a microplate reader 1 according to a first embodiment during insertion of a microplate 2 into the sample chamber 12 which is preferably configured as a chamber which can be closed in a lightproof manner. This microplate reader 1, which is in particular suitable for use in the method according to the invention, comprises a receiving device 4 for receiving at least one microplate 2 with wells 3 containing biological cells or cell cultures. This receiving device 4 is preferably configured to be retractable from the sample chamber 12 of the microplate reader to such an extent that at least one microplate 2 can be inserted by hand or by means of a microplate handling robot (both not shown) into this receiving device 4 or can be removed therefrom. The receiving device 4 is already partially inserted here because specifically one microplate 2 is being inserted into the microplate reader 1. During the insertion or ejection of a microplate, a flap 18 is preferably opened which, in the closed state, preferably closes the sample chamber 12 in a lightproof manner so that no light influencing the investigations can pass from the surroundings into the sample chamber 12.

In addition to receiving at least one microplate 2, this receiving device 4 is used for positioning the microplate(s) 2 with wells 3 containing the biological cells or cell cultures with respect to action sources 5',5",5''' and with respect to measuring devices 6,7,8 of the microplate reader 1.

The microplate reader 1 depicted here further comprises at least one action source 5',5",5''' for bringing about an interaction between at least one of these action sources 5',5",5''' and biological cells or cell cultures in specific wells 3 of the microplate(s) 2 and for bringing about or producing a measurable signal. These action sources are known to every person skilled in the art and are preferably selected from a group which comprises a light source 5' for exciting fluorescence in or on biological cells in wells 3 of these microplate(s) 2. Other action sources known per se are preferably selected from a group comprising a light source 5' for transilluminating biological cells or cell cultures in wells (3) of this/these microplate(s) (2). Such light sources are, for example, selected from a group which comprises arc lamps, flashlamps, incandescent lamps (such as, for example, halogen lamps), lasers, laser diodes and light-emitting diodes (LEDs). The corresponding wavelengths for exciting fluorescence and the corresponding fluorophors and their emission characteristics are also known to the person skilled in the art and are selected according to application. The non-invasive transillumination of cells or cell cultures to detect the absorbance and the light sources used for this are also familiar to every person skilled in the art.

Additional action sources known per se are preferably selected from a group comprising a current source 5" and therefore also an impedance measuring device for measuring an impedance or impedance variation as a function of an attachment or rearrangement of biological cells or cell cultures in wells 3 of this/these microplate(s) 2. Such action sources, which is preferably an alternating current source whose electrical flux can be varied according to a sine function in the range between 20 and 100,000 Hz, where the alternating current source comprises an initial resistance, are known to the person skilled in the art, for example, from the work of Giaever & Keese ("Micromotion of mammalian cells measured electrically", PNAS 1991 Vol. 88: 7896-7900), incorporated herein in its entirety. Preferably used are microplates 2 with specific wells 3 whose well bottoms 16 are at least partially occupied with electrodes 17',17", where the electrodes 17',17" are preferably configured to be contactable with a corresponding current source 5" of the microplate reader 1. For this contacting, electrical contacts 23',23" can be attached to the inner sides of the well walls and the electrodes 17',17" are configured so that they can be brought into contact in this way with contact sensors 27 of the alternating current source, i.e. with the impedance measuring device 5".

Action sources likewise known per se are preferably selected from a group which comprises a liquid source 5''' for triggering luminescence in or on biological cells or cell cultures in wells 3 of this/these microplate(s) 2. The liquid source 5''' is preferably selected from a group which comprises single injectors and multiple injectors for example, for the injection of activator reagents to the cells or cell cultures in specific wells 3 of the microplates 2. Such liquid sources 5''' or injectors, the luminescence-triggering reagents used there, and the wavelengths of the luminescence produced, for example, by cells or their metabolic products are likewise known to the person skilled in the art. In addition, stop agents or nutrients, for example, can be added to the biological cells or cell cultures in the wells 3 of microplates 2 by means of such injectors in order to influence cell growth or cell multiplication.

The microplate reader 1 according to the invention additionally comprises at least one measuring device 5",6,7,8 for detecting at least one integral signal that has been brought about or produced by the action source(s) 5',5",5''' in or on biological cells or cell cultures in the specific wells 3 of the microplate(s) 2. Such measuring devices are preferably selected from a group which comprises photomultipliers, photodiodes, photodiode arrays, avalanche diodes and phase-sensitive lock-in amplifiers. The measuring devices 6,8 and light sources 5' or the optical input and/or output thereof are preferably coupled via light guides 28 such as optical fibers or optical fiber bundles. The sample chamber 12 shown in FIG. 1 is configured to be lightproof.

The microplate reader 1 according to the invention is in particular characterized in that it also comprises an illumination source 9 for illuminating and an imaging camera 10 for imaging the cells or cell cultures in these specific wells 3 of the microplate(s) 2. It is especially preferred that the microplate reader 1 comprises a microscope optics 19 and an imaging camera 10 coupled optically thereto for creating microscope images of biological cells or cell cultures in the specific wells 3 of the microplate(s) 2. Especially preferred is a microplate reader 1 according to the invention in which a module with imaging properties is integrated so that biological cells and cell cultures which are located, for example, on the bottom of the microplate wells can be visualized with microscopic resolution. This imaging module comprises an illumination unit which allows the use of different illumination and imaging modes such as light-field illumination, dark-field illumination and oblique illumination. Additional modes which allow the recording of phase contrast or fluorescence images are also feasible. The images are preferably recorded by means of microscope optics 19 with a digital camera which is fitted with a CMOS or CCD sensor.

The preferred imaging system additionally comprises an autofocus device where a movement of the receiving device 4 in the direction of the optic axis 20 of the imaging camera 10 can be used when using medium apertures to achieve a moderate resolution. The representation of individual cells and cell cultures is preferred, where even smaller particles or cell structures can be imaged. Particularly preferred is the imaging of the number of these biological cells, where particular attention is paid to the adherence of the individual cells, i.e. the adhesion of the cells to the inner surfaces of the wells 3 and the morphology of these cells. Quite especially preferred is the imaging of the adherence, confluence or morphology of cell cultures in the wells 3 of microplates 2, where the term confluence of cell cultures on the inner surfaces of a microplate well 3 reproduces the ratio of the surface covered by a cell culture to the still free surface of the inner surface of these microplate wells which can be occupied by cells.

The microplate reader 1 according to the invention is additionally characterized in that it comprises an internal or integrated processor 11' (cf. FIGS. 2 and 3) or is configured to be connectable to an external processor 11" (cf. FIG. 1). Such a processor 11' can thus be a microprocessor integrated in the electronic controller of the microplate reader 1. It is alternatively also provided to use the processor 11" of a personal computer provided. It is important that the processor 11',11" is configured for comparing each of the detected integral signals with the image of the biological cells in the corresponding wells 3 of the microplate(s) 2 and for relating these integral signals to the imaged number, adherence, confluence or morphology of these biological cells or cell cultures. Preferably such a processor 11',11" is made capable of carrying out this work by activating suitable image processing software and by activating a suitable signal processing software.

The method executed with the aid of this microplate reader for investigating biological cells comprises the following steps:

Receiving at least one microplate 2 with wells 3 containing biological cells or cell cultures with a receiving device of the microplate reader 1. Usually only one microplate having the dimensions of a standard microplate as has been specified by the Society for Biomolecular Sciences (SBS) and the American National Standards Institute (ANSI) is inserted in the receiving device 4. Unlike the diagram in the appended figures, however, two or more microplates can also be received and trans-ported or positioned by the same or different receiving devices 4 of the microplate reader 1. In this case, the receiving device 4 is preferably configured as a frame which comprises stops against which a received microplate 2 is held in a defined position by means of spring-mounted pressing means. Particularly preferred here are pressing means which can be brought by hand or by a robot arm of a microplate handling robot into an open position for insertion or removal of a microplate. The receiving device 4 is preferably movable in an X direction, i.e. preferably horizontally and at right angles to the flap 18 by means of a motor.

Positioning of the receiving device 4 with the wells 3 of the microplate(s) 2 containing biological cells or cell cultures with respect to action sources 5',5",5'" of the microplate reader 1. Thanks to a preferably defined position of the microplate(s) 2 on the receiving device 4, each individual well 3 can be aligned specifically and individually with respect to the axis of action 21 of one of the action sources 5',5",5'". The receiving device 4 is preferably movable in an X direction, i.e. preferably horizontally and at right angles to the flap 18 (cf. arrow in FIG. 1, which is representative for all FIGS. 1-3) and in a Y direction, i.e. preferably horizontally and parallel to the flap 18, by means of a motor so that each well 3 of a microplate can be positioned in a field predefined by these two directions at almost every location. These movements in the X and Y direction are preferably monitored and controlled by a central control unit 22 of the microplate reader 1.

Bringing about an interaction between at least one of these action sources 5',5",5'" and biological cells or cell cultures in specific wells 3 of the microplate(s) 2 to bring about or produce a measurable signal. According to a preferably previously specified protocol, the central control unit 22 of the microplate reader 1 activates the corresponding action source 5',5",5'" when a specific well 3 of the microplate(s) 2 is positioned so that the axis of action 21 of the corresponding action source 5',5",5'" meets the specific well 3 of the microplate(s) 2. Preferably when executing the method according to the invention, the at least one action source 5',5",5'" is selected from a group comprising:

a light source 5' for exciting fluorescence in or on biological cells or cell cultures in wells 3 of these microplate(s) 2;

a light source 5' for transilluminating biological cells or cell cultures in wells 3 of these microplate(s) 2;

a current source 5" for measuring an impedance or impedance variation as a function of an attachment or rearrangement of biological cells or cell cultures in wells 3 of these microplate(s) 2; and a liquid source 5'" for triggering luminescence in or on biological cells or cell cultures in wells 3 of these microplate(s) 2.

In this case, the light source 5' is preferably selected from a group comprising arc lamps, flashlamps, incandescent lamps (such as, for example, halogen lamps), lasers, laser diodes and light-emitting diodes (LEDs) and the current source 5" is preferably an alternating current source whose electrical flux can be varied in accordance with a sine function in the range between 20 and 100,000 Hz, where the alternating current source comprises an output resistance. The liquid source 5'" is preferably selected from a group comprising single injectors and multiple injectors as well as the associated reagent reservoirs and conveying pumps.

During the bringing about of an interaction or directly thereafter, the receiving device 4 with the wells 3 of the microplate(s) 2 containing biological cells or cell cultures is positioned with respect to measuring devices 6,7,8 of the microplate reader 1 and at least one integral signal that is brought about or produced by the action sources 5',5",5''' in or on biological cells or cell cultures in the specific wells 3 of the microplate(s) 2 is detected with at least one of the measuring devices 5",6,7,8:

In the case of fluorescence measurements in specific wells 3 of at least one microplate 2 inserted in the microplate reader 1, it is preferred that the corresponding measuring device 8 for detecting the fluorescence and for recording an integral signal is selected from a group comprising photomultipliers, photodiodes, photodiode arrays and avalanche diodes. The measuring device 8 preferably has a common optic axis 21' with the axis of action 21 of the light source 5' for exciting the fluorescence; where the light source 5' and the measuring device 8 or the optical input and output thereof (cf. FIG. 1) are preferably disposed above (top excitation/top reading) or light source 5' and measuring device 8 are disposed below (bottom excitation/bottom reading) the inserted microplate 2. Small deviations of the axis of action 21 from the optic axis 21' are tolerable.

In the case of luminescence measurements in specific wells 3 of at least one microplate 2 inserted in the microplate reader 1 it is preferred that the corresponding measuring device 7 for detecting the luminescence and for recording an integral signal is selected from a group comprising photomultipliers, photodiodes, photodiode arrays and avalanche diodes. The measuring device 7 preferably has a different optic axis 21' from the axis of action 21 of the liquid source 5' for triggering the luminescence; where the liquid source 5''' is preferably disposed above and measuring device 7 is preferably also disposed above the inserted microplate 2.

In the case of absorbance measurements in specific wells 3 of at least one microplate 2 inserted in the microplate reader 1 it is preferred that the corresponding measuring device 6 for detecting the absorbance and for recording an integral signal is selected from a group comprising photomultipliers, photodiodes, photodiode arrays and avalanche diodes. The measuring device 6 preferably has a common optic axis 21''' with the axis of action 21 of the light source 5' for exciting the fluorescence; where the light source 5' is preferably disposed above and the measuring device 6 or its optical input (cf. FIG. 1) is preferably disposed below the inserted microplate 2.

In the case of measurements of an impedance or impedance variation caused by attachment or rearrangement of biological cells or cell cultures in specific wells of at least one microplate 2 inserted in the microplate reader 1 and for detecting a corresponding integral signal, a measuring device is preferred which is integrated in the current source 5" of the microplate reader 1 and which comprises a phase-sensitive lock-in amplifier. Current source 5" and impedance measuring device 5''' are preferably disposed above the inserted microplate 2.

The method according to the invention for investigating biological cells or cell cultures in a microplate reader 1 is characterized on the one hand in that the biological cells or cell cultures in the specific wells 3 of the microplate(s) 2 are illuminated with the illuminating source 9 of the microplate reader 1, where an integral signal is detected in these specific wells 3 previously or thereafter by means of a measuring device 6,7,8. The method according to the invention for investigating biological cells or cell cultures in a microplate reader 1 is characterized on the other hand in that images of the biological cells or cell cultures in these specific wells 3 of the microplate(s) 2 are created with an imaging camera 10 of the microplate reader 1. In particular, the method according to the invention for investigating biological cells or cell cultures in a microplate reader 1 is characterized however in that each of the detected integral signals is compared with the previously or subsequently recorded image of the biological cells in the corresponding wells 3 of the microplate(s) 2 by means of a processor 11', 11" and is related to the imaged number, adherence, confluence or morphology of these biological cells or cell cultures.

Figure 2:
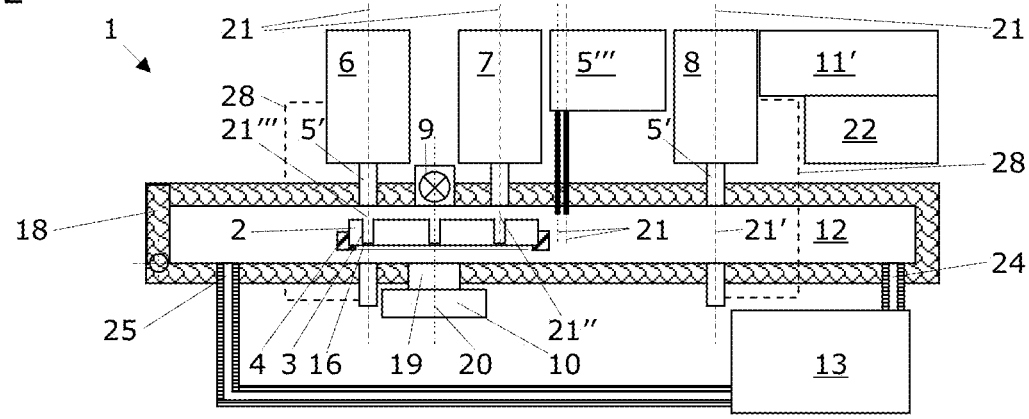
FIG. 2 shows a vertical section through a microplate reader according to a second embodiment during detection of integral signals in selected microplate wells or during microscopic imaging of microplate wells in a sample chamber which is preferably configured as an isolating chamber which can be closed in a lightproof and gastight manner.

FIG. 2 shows a vertical section through a microplate reader 1 according to a second embodiment when detecting integral signals in selected wells 3 of microplates 2 or during microscopic imaging of microplate wells 3 in a sample chamber 12 preferably configured as an isolating chamber which can be closed in a lightproof and gastight manner. Whereas in the first embodiment of FIG. 1, only the avoidance of perturbing ambient light has priority, this second embodiment is directed towards providing a specially suited atmosphere to the cells or cell cultures in the wells 3 of microplates 2 in addition to avoiding perturbing ambient light.

The microplate reader 1 preferably comprises a controller 13 by which means a controlled atmosphere is produced in the sample chamber 12 of the microplate reader 1 configured as an isolated chamber, whereby the concentration of gases present, which are selected from a group comprising oxygen, nitrogen, carbon dioxide and carbon monoxide, is regulated or held in a specific range of values. This controller 13 can be integrated in the microplate reader 1 or provided with this or placed thereon. For example, an $O_2$ sensor for measuring and controlling the oxygen content of the gas atmosphere around the wells 3 containing cells or cell cultures of microplates 2 inserted in this microplate reader 1 and a $CO_2$ sensor for measuring and controlling the carbon dioxide content of this gas atmosphere are disposed in the sample chamber 12. Preferably gas inlets 24 and gas outlets 25 are provided, which pass through the thermally insulated walls or bottom of the sample chamber 12 and are connected or can be connected to the controller 13. A fan (not shown) or other mixing devices can be provided in the sample chamber 12 for moving and mixing and distributing the gases present in the sample chamber.

In the case of a separate controller 13, this is preferably connected directly to the required pressure cylinder for the gases used. The corresponding valves and throttles for the required gas connections are installed in this separate controller 13 (not shown). Alternatively the valves and throttles on the gas pressure cylinders can also be used, where these valves are preferably configured as electrically controlled magnetic valves (of the currentless closed type). Not shown in FIG. 2 among other things are the control elements, display elements and power supplies for the controller 13 which is separate or built into the microplate reader 1 and the microplate reader 1 itself.

The control unit preferably comprises a computer 28 with the corresponding software; in this case the computer 28 can be connected to a central computer 29 of the microplate reader 1 (cf. FIG. 1), can be connectable (e.g. accommodated in a separate housing 17') or can be integrated in this central computer 29 of the microplate reader 1 (not shown).

It can be provided that nitrogen ($N_2$) and/or carbon dioxide ($CO_2$) is used for displacing the ambient air in the sample chamber 12, where appropriate pressure cylinders are provided. These pressure cylinders are fitted as usual with control valves and throttles known per se in order to adjust the required delivery pressure for these gases. Alternatively to this, such process gases can also be obtained from other sources (e.g. from service lines). In addition to nitrogen and carbon dioxide (combined with corresponding gas detectors in the sample chamber 12), other gases can also be used to generate a defined fraction of the atmosphere normally prevailing in the sample chamber. Paying attention to the precautionary measures which may be applicable, other gases such as, for example, noble gases or inert gases (e.g. argon) or also reactive or toxic gases (e.g. oxygen, carbon monoxide, hydrogen sulphide or sulphur dioxide) can thus be introduced into the sample chamber 12 of the microplate reader 1 via at least one gas inlet 24 for producing a known composition of the gas atmosphere above the wells or in the surroundings of the wells 3 of microplates 2 inserted in this microplate reader 1. Preferably the controller is equipped with sufficient gas lines and control valves so that more complex gas compositions with a plurality of gas components are made possible.

Mention should be made of the $CO_2$ sensor SenseAir® $CO_2$ Engine® ICB, Part No.: 033-9-0001 from SenseAir AB in SE-820 60 Delsbo, Sweden, as representative of suitable $CO_2$ sensors. Mention should be made of the $O_2$ sensor Pewatron FCXMEP2-F—CH oxygen module from Pewatron AG in CH-8052 Zürich, Switzerland as representative of suitable $O_2$ sensors.

Preferably, the sample chamber 12 configured as an isolating chamber is equipped with an air cooling system which is connected to the sample chamber 12 via supply and discharge lines. The controller 13 can additionally be configured as such an air cooling system and comprise cooling elements, e.g. in the form of Peltier elements. In particularly preferred microplate readers 1, a controlled atmosphere can be produced in the sample chamber 12 configured as isolating chamber whereby parameters selected from a group comprising temperature, relative humidity and total pressure are each regulated or held in a specific range of values. Preferably the relative humidity is held or regulated in an end moisture region so that there is no risk of condensation of water vapor at surfaces in the sample chamber and also no drying of the cells or cell cultures.

In connection with the present invention, cell cultures, biological cell accumulations or single cells separated from these or obtained in some other way are designated as cells, where these cells comprise microorganisms and fungi as well as animal and vegetable eukaryotic cells.

In FIG. 2 specifically one well 3 is located in the region of the optic axis 21''' of the second measuring device 7 for luminescence measurements. Another well 3 is specifically located in the region of the optic axis 20 of the imaging camera 10 and the illumination source 9. Another well 3 of the same microplate 2 is located specifically in the region of the optic axis 21''' of the first measuring device 6 for absorbance measurements. Whereas in FIG. 1 two imaging cameras 10 with appurtenant microscope optics 19 and illumination sources 9 are shown, the second embodiment has only one suitably fitted imaging camera 10.

Figure 3:
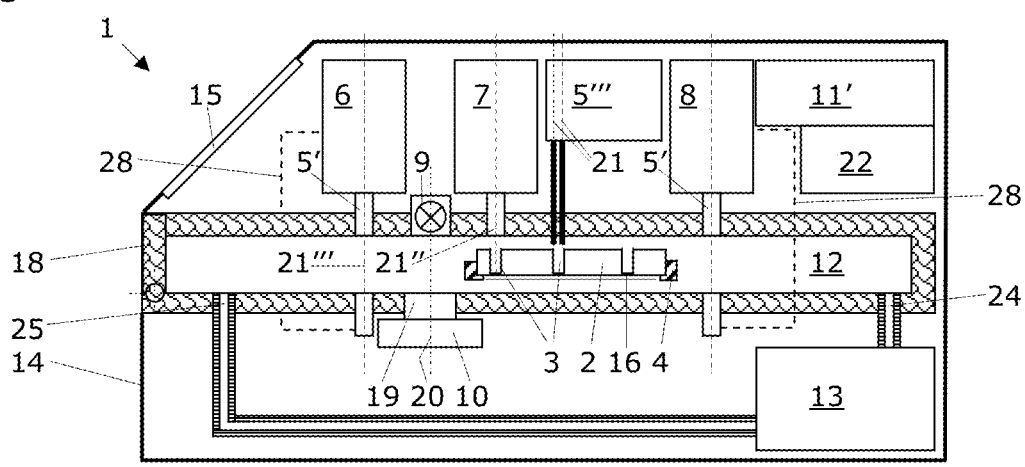
FIG. 3 shows a vertical section through a microplate reader according to a third embodiment during detection of integral signals in selected microplate wells in a sample chamber which is preferably configured as an isolating chamber which can be closed in a lightproof and gastight manner.

FIG. 3 shows a vertical section through a microplate reader 1 according to a third embodiment during the detection of integral signals in selected microplate wells 3 in a sample chamber 12 preferably configured as an isolating chamber which can be closed in a lightproof and gastight manner. This third embodiment of the microplate reader 1 according to the invention has a housing 14 into which the entire microplate reader 1 with all the action sources 5',5'',5''' and measuring devices 6,7,8 is installed. In addition, along with the sample chamber 12 configured as an isolating chamber, a central control unit 22 is also installed in the housing 14 as is also covered by the first two embodiments.

Located in FIG. 3 is specifically one well 3 in the region of the axis of action 21 of the liquid source 5''' which (as also in FIGS. 1 and 2) is fitted with a double injector. Another well 3 is located specifically in the region of the optic axis 21''' of the second measuring device 7 for luminescence measurements. A local arrangement of at least one injector of a liquid source 5''' as close as possible to the optic axis 21'' of the second measuring device 7 is preferred so that the measurement of the luminescence can be made with the smallest possible time difference between injection (triggering of the luminescence) and detection of the luminescence. The optic axis 20 of the imaging camera 10 with the microscope optics 19 and the illumination source 9 is located close to the optic axis 21'' of the second measuring device 7.

The microplate reader 1 preferably comprises a screen 15 for displaying operating states, measurement results, microscope images and for displaying results from the comparison of the detected integral signals with the corresponding images of the biological cells or cell cultures in the respective wells 3 of the microplate(s) (2) and the ratio to the imaged number, adherence, confluence or morphology of these biological cells or cell cultures. The screen 15 is preferably configured as a touch-sensitive screen or touch screen so that it can also be used as an interface for adjusting or varying the operating parameters of the microplate reader 1 and for processing and storing the results produced.

Figure 4:
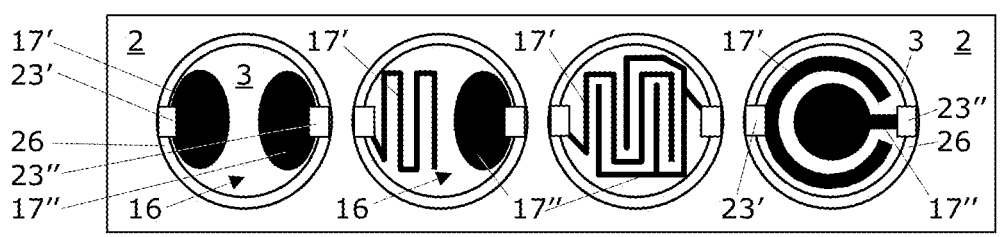
FIG. 4 shows a plan view of microplate wells with exemplary electrodes attached to the well bottom and with exemplary electrode contacts attached to the well walls.

FIG. 4 shows a plan view of microplate wells 3 with exemplary electrodes 17',17'' attached to the well bottom 16 and with exemplary electrical contacts 23',23'' attached to the well walls. These electrodes 17',17'' and electrical contacts 23',23'' are preferably made of gold or a gold alloy and are applied by means of sputtering or another suitable coating method to the well bottom 16 or to the inner surface and preferably to the well edge 26. In particular, the electric contacts 23',23'' extending as far as the well edge 26 can be connected relatively simply to the contact sensors 27 of the current source 5'' by moving the microplate 2 with the receiving device 4 towards the current source 5'', that is preferably with a corresponding motor drive in a vertical Z direction (cf. arrow in FIG. 1, representative of all FIGS. 1-3) until the contact sensors 27 of the current source 5'' are contacted with the electrical contacts 23',23''. Preferably therefore the receiving device 4 with the microplate(s) 2 containing biological cells or cell cultures is moved during positioning in at least one direction of movement where this direction of movement is selected from a group comprising an X, a Y and a Z direction in a three-dimensional coordinate system. For bringing about an interaction between at least one of the action sources 5',5'',5''' and biological cells or cell cultures in wells 3 of the microplate(s) 2 and also for detecting a corresponding integral signal with at least one of the measuring devices 6,7,8 or the current source 5'', the receiving device 4 with the microplate(s) 2 containing biological cells or cell cultures can preferably be moved in at least one direction of movement where this direction of movement is selected from a group comprising an X, a Y and a Z direction in a three-dimensional coordinate system.

FIG. 4 shows a selection of exemplary electrodes 17',17'' whose material influences the adherence, confluence or morphology of biological cells or cell cultures as little as possible and preferably not at all. As shown, for example, the electrodes 17',17" can be configured to be the same or different and completely cover a surface or only cover an area or array.

The same reference numbers and signatures indicate comparable features even if these are not described for all figures and all reference numbers. Any combinations of the features which have been described and/or shown belong to the scope of the present invention.

Particularly preferred as fluorescence measurements in connection with the present invention are inter alia measurements of the fluorescence intensity; time resolved fluorescence measurements; measurement of the fluorescence polarization and measurement of the fluorescence lifetime.

In addition to measurement of the luminescence intensity, in particular kinetic measurements on cells and cell cultures by means of the luminescence and also the detection of the luminescence kinetics are of interest in connection with the present invention.

The FIG. 5 shows a schematic representation of the light path of the transillumination through a well 3 of a microplate 2. There, the FIG. 5A shows a conventional transillumination with sketched path of the transmitted light beam bundle 29. This classic type of illumination for bright field microcopy is called Köhler's illumination.

As a light source 5', an LED is used, the light 29 of which is collected by a collector lens 31 and imaged in the focal plane of the condenser lens 32. The condenser lens focuses the light 29 in the sample plane and illuminates with high intensity the small sample region that is imaged on the CCD or CMOS chip 35 of the camera 10 with increased magnification using the objective 34. The luminous filed aperture 33 limits the illuminated region in the sample plane of the wells 3 and fulfills the function to minimize the load of the sample by the light and heat irradiation and to minimize stray light. The aperture diaphragm 30 which is placed after the light source 5' defines the numeric aperture of the illumination light cone 29 between the condenser lens 32 and the sample plane in the well 3. With a small opening of the aperture diaphragm 30, the illumination light cone 29 shows a small opening angle. With a large opening of the aperture diaphragm 30 however, the illumination light cone 29 shows a large opening angle. Usually, the aperture diaphragm 30 is placed in the focal plane of the condenser lens 32. In the embodiment shown however, the aperture diaphragm 30 is placed in the plane of the light source, which is regarded as equivalent with respect to the optical image. The shown arrangement of the aperture diaphragm 30 provides for the possibility of utilizing a motorized aperture wheel (not shown), which comprises a number of aperture diaphragms 30 with different size and shape.

Contrary to a conventional microscopy sample, which is thin and two-dimensional, and which is located in-between two glass plates (a microscopy slide and a cover slip), the illumination light 29 needs to penetrate the entire liquid volume prior to reaching the sample plane that is located at the bottom of the well 3. The surface of the liquid is considerably bent through adhesion effects, i.e. a meniscus is built up which acts like a diverging lens.

The FIG. 5C shows a conventional transillumination with sketched path of a transmitted light beam 29. When using a small opening of the aperture diaphragm 30 (cf. FIG. 5A), the border beams that usually illuminate the outer region of the sample area imaged by the objective 34 are deflected to the outside and do not impinge on the outer region of the well bottom or as shown, cannot be captured by the objective 34 and recorded by the imaging chip 35. Therefore in the resulting image, there results a dramatic intensity decrease towards the outside. This intensity decrease can only partially be mathematically compensated by the consecutive image processing. The resulting intensity decrease leads to lesser reliable counting or determination of confluence of the cells in the outer regions of the well.

The FIG. 5B shows an inventive transillumination with sketched path of the transmitted light beam bundle 29. The setup for this transillumination with high numeric aperture is identical to that for the normal illumination (cf. FIG. 5A), except for the size of the opening of the aperture diaphragm 30. Here, the opening size of the aperture diaphragm 30 is considerably enlarged for enlarging the opening angle of the illumination cone 29.

The FIG. 5D shows an inventive transillumination with sketched path of a transmitted light beam 29. The border beams of the illumination cone 29 impinge under a larger angle on the curved surface of the liquid, they undergo a weaker deflection towards the outside and they thus illuminate also the border regions of the well bottom in a way that the light 29 may enter the objective 34 of the camera 10 and can be detected by the imaging chip 35. This results in a considerably weaker intensity gradient. The contrast is better even in the outer regions of the well 3 and now, reliable counting or determination of confluence of the cells also in the outer regions of the well is possible.

The FIG. 6 shows pictures of a well 3 in transillumination. Here, the stitched together images of one well that contains a cell culture are shown as a mosaic. Among others, the brightness of the image depends on the exposure time. The brightness for each single image has been optimized in its contrast using imaging software. The global brightness distribution over the bottom of the well 3 leads to brightness steps at the contact sites of the single images.

Figure 6A:
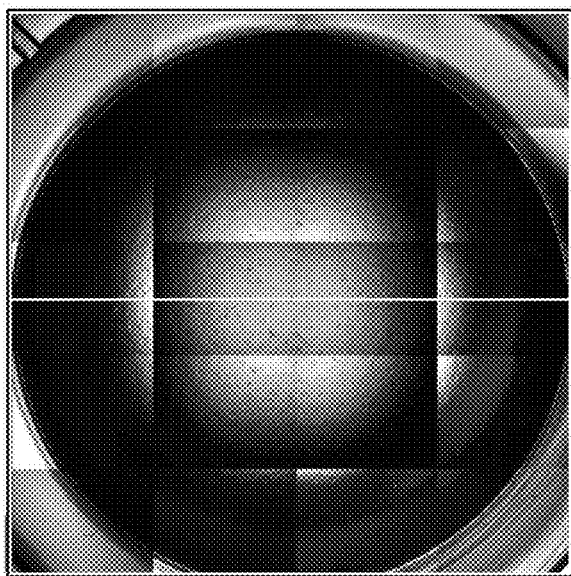
FIG. 6A shows the result of conventional illumination.

The FIG. 6A shows the result of a conventional illumination. The single images have been recorded with small aperture diaphragm 30 (cf. FIGS. 5A and 5C), the decrease of brightness towards the border is pronounced.

Figure 6B:
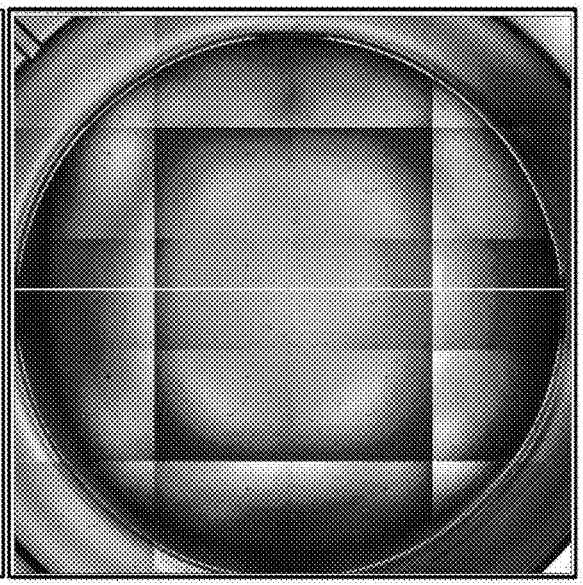
FIG. 6B shows the result of inventive illumination.

The FIG. 6B shows the result of an inventive illumination the same well 3 as illuminated with larger aperture diaphragm 30 (cf. FIGS. 5B and 5D). It is evident that evaluatable brightness values are present until the well border.

The FIG. 7 shows the distribution of the intensity across a whole diameter of the wells (see bright line) in the pictures of FIG. 6. There is shown an intensity cross section through the two mosaics. The steps result from the differences in the exposure time of the single images.

Figure 7A:
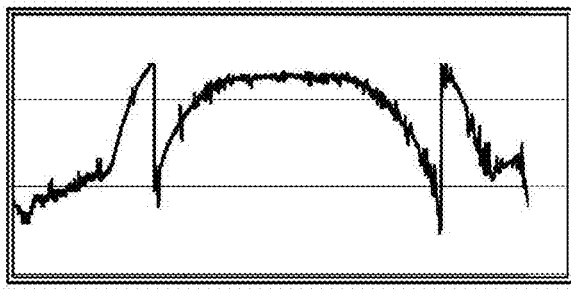
FIG. 7A shows the intensity distribution at conventional illumination.

The FIG. 7A shows the intensity distribution at conventional illumination with small aperture diaphragm 30 (cf. FIGS. 5A and 5C). It can be seen that at conventional illumination in the outer regions, only very low intensity values can be achieved which lay in the range of camera noise.

Figure 7B:
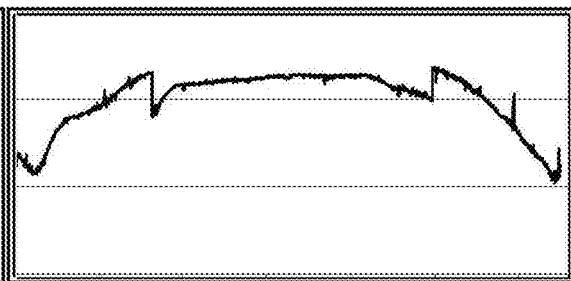
FIG. 7B shows the intensity distribution at inventive illumination.

The FIG. 7B shows the intensity distribution at inventive illumination with large numeric aperture 30 (cf. FIGS. 5B and 5D). It appears obvious that the gradients are formed much weaker. The intensity steps from one single image to the other are much smaller because the global brightness differences are weaker through compensating the exposure time.

Figure 8:
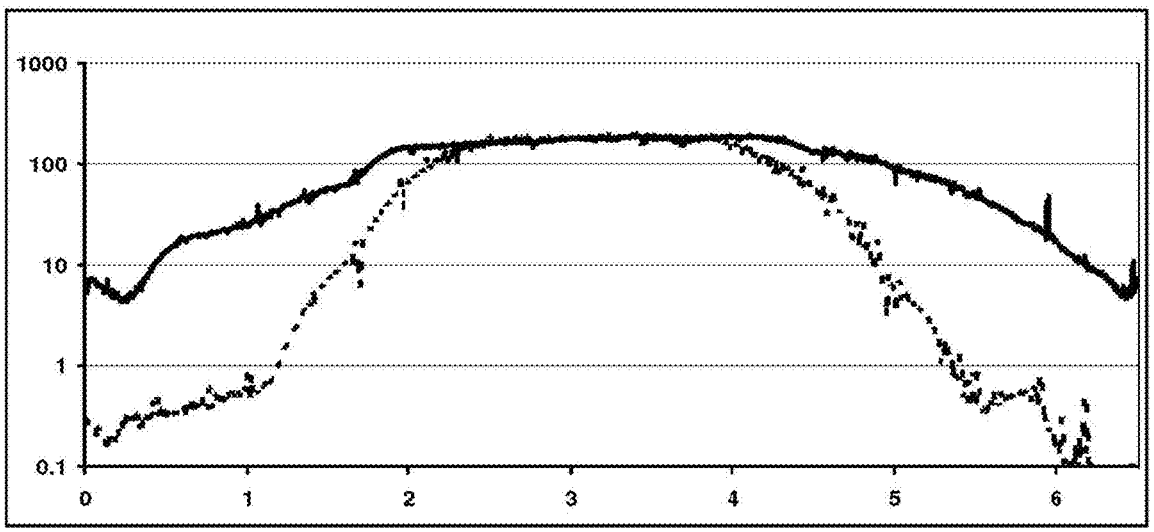
FIG. 8 shows a comparison of the two illustrations of FIGS. 7A and 7B after normalization of the illumination in each case.

The FIG. 8 shows a comparison of the two illustrations of FIGS. 7A and 7B after normalization of the illumination in each case. For this direct comparison of the results of conventional and inventive imaging, the differences in the exposure time has been normalized. In this graph, the abscissa indicates positions on the well bottom in distances of 1 mm and the ordinate indicates intensity values (grey values) on a logarithmic scale. The dashed line represents the conventional illumination and the bold line represents the inventive illumination with large aperture diaphragm. The decease of the intensity towards the well border at inventive illumination with large aperture diaphragm amounts to about 20 fold. In contrast, the decease of the intensity towards the well border at normal, conventional illumination amounts to about 500 fold. This leads at an illumination with large aperture diaphragm to utilizable Signals in the border region, whereupon normal illumination is not possible as shown. Regarded as a small numeric aperture is an aperture diaphragm 30 with an opening in the range of 1-3 mm and regarded as a large numeric aperture is an aperture diaphragm 30 with an opening in the range of 5-9 mm. Of special preference is an opening diameter of 9 mm of the aperture diaphragm 30 at large numeric aperture.

REFERENCE LIST

| | |
|---|---|
| 1 | Microplate reader |
| 2 | Microplate |
| 3 | Well |
| 4 | Receiving device |
| 5', 5", 5''' | Action sources |
| 5' | Light source |
| 5" | Current source; impedance measuring device |
| 5''' | Liquid source |
| 6 | First measuring device for absorbance measurements |
| 7 | Second measuring device for luminescence measurements |
| 8 | Third measuring device for fluorescence measurements |
| 9 | Illumination source |
| 10 | Imaging camera |
| 11' | Internal processor |
| 11" | External processor |
| 12 | Sample chamber |
| 13 | Controller |
| 14 | Housing |
| 15 | Screen |
| 16 | Well bottom |
| 17', 17" | Electrodes |
| 18 | Flap |
| 19 | Microscope optics |
| 20 | Optic axis of 10 |
| 21 | Axis of action |
| 21' | Optic axis of 8 |
| 21" | Optic axis of 7 |
| 21''' | Optic axis of 6 |
| 22 | Central control unit |
| 23', 23" | Electrical contacts |
| 24 | Gas inlets |
| 25 | Gas outlets |
| 26 | Well edge |
| 27 | Contact sensor |
| 28 | Light guide |
| 29 | Light, light beam, light beam bundle |
| 30 | aperture diaphragm |
| 31 | collector lens |
| 32 | condenser lens |
| 33 | luminous filed aperture |
| 34 | camera objective |
| 50 35 | CCD, CMOS chip |

The invention claimed is:
1. A method of measuring a cell activity of biological cells or cell cultures using a microplate reader, the method comprising the steps:

a) providing a microplate reader which comprises
   a measuring device having a first optical axis and defining a first measuring region along said first optical axis;
   an imaging device separate to the measuring device, the imaging device having a separate, second optical axis parallel to the first optical axis of the measuring device, the imaging device comprising an illumination source, microscope optics and an imaging camera coupled thereto, said imaging device defining a first imaging region along said second optical axis in between said illumination source and said microscope optics, wherein said first imaging region is separate from said first measuring region; and
   a receiving device for receiving at least one microplate with wells comprising a bottom and for positioning an inserted microplate within the microplate reader with respect to the first optical axis of the measuring device and with respect to the second optical axis of the imaging device, the receiving device being movable in an X direction and a Y direction by means of a motor;
   a central control unit for controlling the microplate reader;
   a processor which is integrated into the central control unit, and which comprises an image processing software and a signal processing software; and
   a housing, into which the measuring device, the imaging device, the receiving device, the central control unit and the processor are installed; and
   inserting at least one microplate with wells containing biological cells or cell cultures into said receiving device;
b) under the control of the central control unit: positioning a specific microplate well of said wells in said first measuring region by moving the receiving device in an X and/or Y direction, and quantitatively measuring a total intensity of an integral signal using the measuring device, wherein said integral signal is integral with respect to the entire specific microplate well and wherein a variation of the total intensity of said integral signal depends at least on a variation of a cell activity;
c) under the control of the central control unit: positioning said specific microplate well in said first imaging region by moving the receiving device in an X and/or Y direction, transilluminating said specific microplate well using the illumination source of the imaging device and creating a bright-field dark-field, or phase contrast image of adherent biological cells or cell cultures on the bottom of said transilluminated well and recording said image using the imaging device;
d) determining a confluence of said adherent biological cells or cell cultures on the imaged bottom of said specific microplate transilluminated well based on the image recorded in step c) using the image processing software of the processor;
e) relating the measured total intensity of the integral signal with respect to said specific microplate well according to step b) to the determined confluence of the adherent biological cells or cell cultures in said specific microplate well according to step d), and normalizing said total intensity with said determined confluence using the signal processing software of the processor, thereby producing an unbiased and comparable measuring result reflecting said cell activity of the adherent biological cells or cell cultures in said specific microplate well.

2. The method of claim 1, wherein the receiving device together with the wells of the at least one inserted microplate is positioned with respect to action sources of the microplate reader and an interaction between at least one of these action sources and said biological cells or cell cultures in said specific microplate well of the inserted microplate is brought about for bringing about or generating the integral signal.

3. The method of claim 2, wherein the at least one action source is selected from a group which comprises:
an action light source for exciting fluorescence in or on biological cells or cell cultures in said specific microplate well;
an action light source for transilluminating biological cells or cell cultures in said specific microplate; and
an action liquid source for triggering luminescence in or on biological cells or cell cultures in said specific microplate well.

4. The method of claim 1, wherein the integral signal is selected from a group which comprises:
fluorescence excited in or on biological cells or cell cultures in said specific microplate;
luminescence triggered or existing in or on biological cells or cell cultures in said specific microplate well; and
absorbance brought about by biological cells or cell cultures in said specific microplate well.

5. The method of claim 3, wherein the action light source for generating the integral signal is selected from the group consisting of arc lamps, flashlamps, incandescent lamps, lasers, laser diodes and light-emitting diodes.

6. The method of claim 3, wherein the action liquid source for triggering the integral signal is selected from the group consisting of a single injector and multiple injectors.

7. The method of claim 1, wherein the measuring device for detecting an integral signal is selected from the group consisting of photomultipliers, photodiodes, photodiode arrays, avalanche diodes and phase-sensitive lock-in amplifiers.

8. The method of claim 1, wherein during positioning the receiving device with the at least one inserted microplate is moved in at least one direction of movement, wherein this direction of movement is selected from a group comprising an X, a Y, and a Z direction in a three-dimensional coordinate system.

9. The method of claim 1, wherein said specific microplate well of the at least one inserted microplate is investigated in a lightproof sample chamber of the microplate reader.

10. The method of claim 1, wherein the wells of the at least one inserted microplate are exposed to a controlled atmosphere in a sample chamber of the microplate reader, the sample chamber being thermally insulated.

11. The method of claim 9, wherein the at least one inserted microplate is held by the receiving device in the lightproof sample chamber of the microplate reader at least during the execution of process steps b) to c).

12. The method of claim 10, wherein the at least one inserted microplate is held by the receiving device in the thermally insulated sample chamber of the microplate reader at least during the execution of process steps b) to c).

13. The method of claim 11, wherein the adherent biological cells or cell cultures in said specific microplate well are transilluminated with the illumination source of the imaging device in the sample chamber of the microplate reader being thermally insulated, and the adherent biological cells or cell cultures in said specific microplate well are recorded with the imaging camera via a microscope optics of the imaging device.

14. The method of claim 12, wherein the adherent biological cells or cell cultures in said specific microplate well are transilluminated with the illumination source of the imaging device in the sample chamber of the microplate reader being thermally insulated, and the adherent biological cells or cell cultures in said specific microplate well are recorded with the imaging camera via a microscope optics of the imaging device.

15. The method of claim 1, wherein microscope optics comprising an aperture diaphragm with large numeric aperture image the adherent biological cells or cell cultures transilluminated with the illumination source of the imaging device of the microplate reader.

16. The method of claim 1, wherein at least the process steps b) to c) are carried out in an automated manner.

17. The method of claim 15, wherein the aperture diaphragm has an opening in the range of 5-9 mm.

18. The method according to claim 1, wherein the method comprises the steps:
performing step a);
selecting wells of said at least one microplate; and
performing steps b) to e) for each one of said selected wells, wherein each one of said selected wells in turn has the role of said specific microplate well.

* * * * *